(12) United States Patent
Bass

(10) Patent No.: US 6,585,673 B1
(45) Date of Patent: Jul. 1, 2003

(54) PRESSURE BINDER AND PACK POSITIONER

(75) Inventor: Andrea Bass, Elgin, IL (US)

(73) Assignee: Debbie M. Sauder, Elgin, IL (US); part interest ( * ) Notice: Subject to any disclaimer, the term of this patent is extended or adjusted under 35 U.S.C. 154(b) by 0 days.

(21) Appl. No.: 10/071,033

(22) Filed: Feb. 8, 2002

(51) Int. Cl.$^7$ ................................................ A61F 13/00
(52) U.S. Cl. ............................ 602/60; 602/61; 602/75; 2/44; 2/312; 128/845
(58) Field of Search .................................. 602/19, 41–42, 602/53, 60–66, 74–75; 2/44, 312, 455, 456, 464, 467, 308, 310, 319, 320, 913, 915; 128/100.1, 101.1, 845, 846, 869

(56) References Cited

U.S. PATENT DOCUMENTS

| | | | | |
|---|---|---|---|---|
| 3,603,316 A | * | 9/1971 | Lehman | |
| 3,717,143 A | * | 2/1973 | Johnson | |
| 3,888,245 A | * | 6/1975 | Berntson et al. | |
| 4,135,503 A | * | 1/1979 | Romano | |
| 5,007,412 A | * | 4/1991 | DeWall | |
| 5,148,804 A | * | 9/1992 | Hill et al. | |
| 5,179,942 A | * | 1/1993 | Drulias et al. | |
| 5,372,575 A | * | 12/1994 | Sebastian | |
| 5,716,388 A | * | 2/1998 | Petelle | |
| 5,984,885 A | * | 11/1999 | Gaylord, Jr. et al. | |

* cited by examiner

*Primary Examiner*—Nicholas D. Lucchesi
*Assistant Examiner*—Lalita M Hamilton
(74) *Attorney, Agent, or Firm*—Charles F. Meroni, Jr.; Meroni & Meroni, P.C.

(57) ABSTRACT

An elasticized pressure binder and pack positioner comprises a pocket, a pair of elongated elasticized straps, and a pair of elongated extension straps. The pocket has three closed ends and one open end. The open end can be closed by means for closing. The pair of elongated elasticized straps is attached to and extending from one of the three closed ends. There are a pair of hook portions of a hook and loop type fastener structure on the side of the pocket. There is a loop portion of the hook and loop fastener structure at the end of each of the pair of elongated elasticized straps. One side of each of the pair of elongated extension straps is a loop portion of the hook and loop fastener structure. The other side of each of the pair of elongated extension straps is a hook portion of the hook and loop fastener structure.

11 Claims, 6 Drawing Sheets

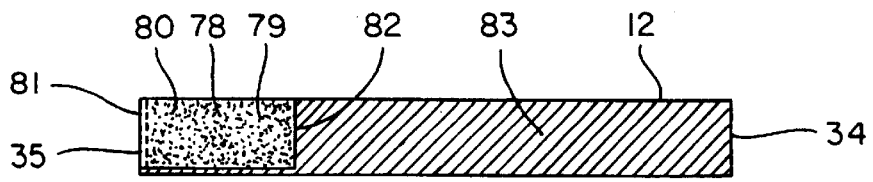
*Fig. 10*
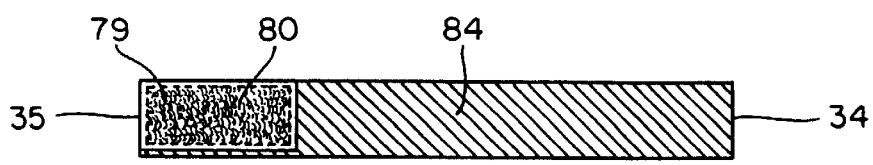
*Fig. 11*
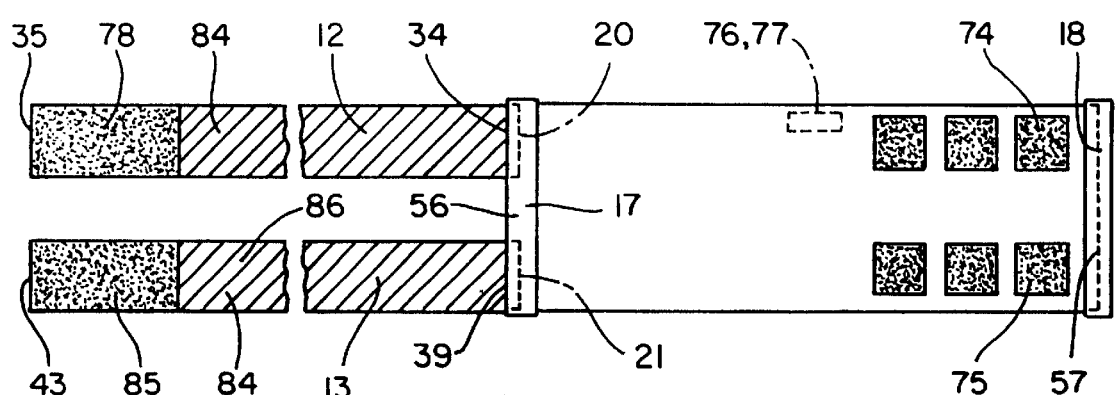
*Fig. 12*
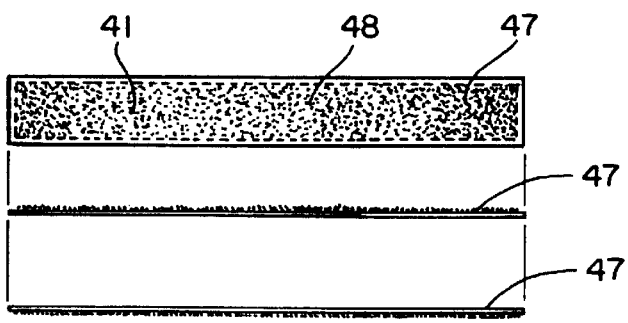
*Fig. 13a*
*Fig. 13b*
*Fig. 13c*

PRESSURE BINDER AND PACK POSITIONER

BACKGROUND OF THE INVENTION

1. Field of the Invention

The present invention relates to a pressure binder, which can also be used as a hot/cold pack positioner. More specifically, the present invention is primarily intended for bodily use by being positioned either over or under a garment to provide comfort support to various selected body parts and also to aid in the faster recovery of various injured body parts.

2. Description of the Prior Art

There are many designs for pack positioners or pressure binders currently found in the prior art. These pack positioners or pressure binders typically include a supporting portions and a fastening portions. The supporting portions is used to support various body parts and the fastening portions is used to fasten the supporting portions in its intended position on various body parts.

When a person is injured, he or she usually needs to secure that injured part in a recommended position for certain period of time in order to aid in the recovery of the injured part. Oftentimes, it is also necessary to add pressure to the injured part or secure a hot/cold pack to the injured part.

Various devices have been created in an attempt to meet these needs. There are usually two primary, intended functions of the pack positioners or pressure binders currently on the market. The first of these primary functions is to bind or fix certain body parts in a recommended position and the second of these primary function is to securely position the intended device to a selected body part. However, as can be discerned from the prior art, it is difficult to comfortably and effectively position a device to a body part and bind the body part securely into a recommended position.

U.S. Pat. No. 4,245,628, which issued to Eichler, discloses a Back Support Device of variable pressure action whereby directed segmental treatment can be carried out and atrophy of back extensors avoided. The Back Support Device comprises a back support bandage with a support pad fastened thereto. The support pad further comprises a substantially rigid fastening plate attached to the support bandage; a rib plate which is arched away from the fastening plate (towards the spinal column) and fastened at its upper and lower ends to the fastening plate; and a foam cushion which takes up the space between the fastening plate and the rib plate. The rib plate has flexible ribs which are separated from each other and arranged parallel to each other. These ribs consist of a resilient material, extend between the two fastened ends of the rib plate and are fastened in the vicinity of the rib plate ends. The rib plate as such and/or the individual ribs thereof may consist of metal or plastic, insofar as this material possesses elasticized resiliency. Thus, for instance, the ribs may consist of flexible, resilient sheet metal and be attached (for example by rivet or solder) to a plastic or metal frame forming the rib plate, but it is advisable to manufacture the rib plate integral with the individual ribs from a single material, such as a steel sheet or a plastic. The latter is preferred because of its lighter weight. With such a one-piece development of the rib plate, the plate is divided into parallel slots in a longitudinal direction between the two fastening ends, which slots terminate in each case in front of the fastening end of the rib plate so that a web is formed in the two fastening ends, which is approximately perpendicular to the ribs, to which web the individual ribs are connected integrally.

U.S. Pat. No. 4,351,325, which issued to Walker, discloses a Hernia Support. The Hernia Support, designed particularly for inguinal hernias, comprises a "roll-on" belt to which a pressure pad for bearing on the area of the hernia is indirectly attached by an arrangement including a rigid stay member. A strap extends from a lower edge of the pad between the wearer's legs to keep the pad pressed against the body by reaction with the rigid stay even when movement tends to displace the adjacent portions of the belt away therefrom (for example when the user sits or stoops).

U.S. Pat. No. 5,154,187, which is issued to Brownlee, discloses an Abdominal Pressure Diffuser, which is an adjustable protective device for positioning on a human body. The Abdominal Pressure Diffuser operates to expand the abdominal region so as to space a garment supporting the belt and/or a belt integrally formed with a garment from the abdominal area in the general area of the groin. The device is of a size which spaces its cushioned ends substantially on either side of the groin area and is positioned between the human body and/or a garment such as an underwear brief. Further, the Abdominal Pressure Diffusers comprises a belt which operates in connection with the abdominal and groin area so as to permit the wearer to sit down with the belt in spaced relation to the body and allow the abdomen to move outwardly, thus preventing pressure on the abdomen and more particularly on the bladder and/or any healing surgical incision in this area such as a prostate, bladder or urethra duct operation would cause.

U.S. Pat. No. 5,207,635, which is issued to Richards, et al., discloses an Orthopedic Device for providing lower back support. The Orthopedic Device provides lower back support for a wearer and includes a flexible flat body, a resilient contoured lumbar support pad of varying thickness secured to the body, and a flexible belt traversing the pad and secured to the body at points beyond the pad. The belt is configured and dimensioned to be secured about the waist of the wearer for positioning the pad on the lumbar region of the wearer.

U.S. Pat. No. 5,600,854, which is issued to Henrekin, discloses an Adjustable Strap Fastener Assembly for a body-encircling hat band, collar or belt, which forms an adjustable loop around a portion of a wearer's body. The Adjustable Strap Fastener Assembly has a body portion comprising an elongate member for encircling the body portion and first and second inter-engageable end portions at opposite ends of the elongate member. One of the end portions is a buckle and the other end portion is a strap for releasable threaded engagement through the buckle with the free end of the strap on the inside of the loop. Secondary fasteners such as mateable strips of VELCRO material are provided on the opposing inner faces of the free strap end and inner face of the loop. The elongate member may be a belt or waistband, a collar for an animal, or a hat band or sweat band of a cap or hat.

Each of these patents discloses a kind of support device. However, none of them can be used as a medical appliance that is capable of providing patients with a comfortable support device which is simple to manufacture and/or use for the purposes herein outlined. Patients, who want to have a medical pack securely positioned on a body part or have a body part securely bound in a recommended position need an improved pressure binder and pack positioner, which is simple in structure, easy to use, and comfortable to wear.

Accordingly, it will thus be seen that an improved pressure binder and pack positioner, which is simple in structure, less expensive to manufacture, easy to use, and comfortable for a user to wear is needed.

Accordingly, it is a principal object of the present invention to provide an improved pressure binder and pack positioner, which is capable of binding a human body part to its intended position with adjustable pressure.

It is a further object of the present invention to provide an improved pressure binder and pack positioner, which is capable of positioning a cold or hot pack at its intended position on various body parts.

It is a still further object of the present invention to provide an improved pressure binder and pack positioner, which is capable of applying adjustable pressure to the selected body part, on which it is applied.

It is a further object of the present invention to provide an improved pressure binder and pack positioner which is easy to manufacture.

It is a still further object of the present invention to provide an improved pressure binder and pack positioner which is simple in structure;

It is a further object of the present invention to provide an improved pressure binder and pack positioner which is light in weight; and It is a still further object of the present invention to provide a method to manufacture such an improved pressure binder and pack positioner.

SUMMARY OF THE INVENTION

According to the present invention, provided is an elasticized pressure binder and pack positioner capable of being comfortably attached to various different parts of a human body. The elasticized pressure binder and pack positioner comprises a pocket, a plurality of elongated elasticized straps, and a plurality of elongated extension straps. The pocket is capable of securely enveloping or pocketing an object. The pocket has a front side and a back side. The front side comprises the hook portion of a hook and loop fastener structure. The elongated elasticized strap has a first strap side, a second strap side, a first strap end and a second strap end. The first strap end is affixed to the pocket, the second strap end extends from the pocket, the first strap side is a first portion of a first hook and loop fastener structure, the second strap side has a second portion of a first hook and loop fastener structure at the second end, the second portion of the first hook and loop fastener structure is capable of attaching to and detaching from the first portion of the side loop and fastener structure. The elongated extension strap has a third strap end, a fourth strap end, a third strap side and a fourth strap side. The third strap side is a first portion of a second hook and loop fastener structure. The fourth strap side has a second portion of the second hook and loop fastener structure at the fourth end. The first portion of the second hook and loop fastener structure is capable of attaching to and detaching from the second portion of the first hook and loop fastener structure at the second strap end. The second portion of the second hook and loop fastener structure is capable of attaching to and detaching from the first portion of the side hook and loop fastener structure.

The present invention further involves a method of manufacturing an elasticized pressure binder and pack positioner capable of comfortably affixing to various different parts of a human body. The method generally comprises:

providing a pocket with an open end and three close ends, the open end has a means for closing, the means for closing is capable of closing the open end, the pocket has a front side and a back side and is capable of securely holding at least a pound of weight;

providing a hook and loop fastener structure, the hook and loop fastener structure has a hook portion and a loop portion;

stitching the hook portion onto the front side, the hook portion can be either a single hook portion or a plurality of hook portions;

providing an elongated elasticized strip, the elongated elasticized strip has a first end and a second end, the elongated elasticized strip can be either a single elongated elasticized strip or a plurality of elongated elasticized strips;

stitching the first end onto one of the three closed ends; and stitching the loop portion onto the second end.

DESCRIPTION OF THE DRAWINGS

Other features of the present invention will become more evident from a consideration of the following detailed descriptions of the patent drawings, as follows:

FIG. 10 is an elevation view of the elongated elasticized strap with a loop portion of a VELCRO strip being stitched across the end of the elongated elasticized strap.

FIG. 11 is an elevation view of the elongated elasticized strap with a loop portion of a VELCRO strip being fully stitched onto the end of the elongated elasticized strap.

FIG. 12 is a fragmentary side view of the elasticized pressure binder and pack positioner with two extension straps.

FIG. 13(a) is a front view of an elongated extension strap.

FIG. 13(b) is a side view of a front piece of the elongated extension strap.

FIG. 13(c) is a side view of a back piece of the elongated extension strap.

DETAILED DESCRIPTION OF THE PREFERRED EMBODIMENT

The present invention is an elasticized pressure binder and pack positioner, which is capable of being comfortably affixed to various different parts of a human body. The present invention can be used as either a pressure binder to provide needed pressure onto various different parts of a human body, or a pack positioner to secure a hot or cold pack to its intended position on various different part of a human body.

Figure 1:
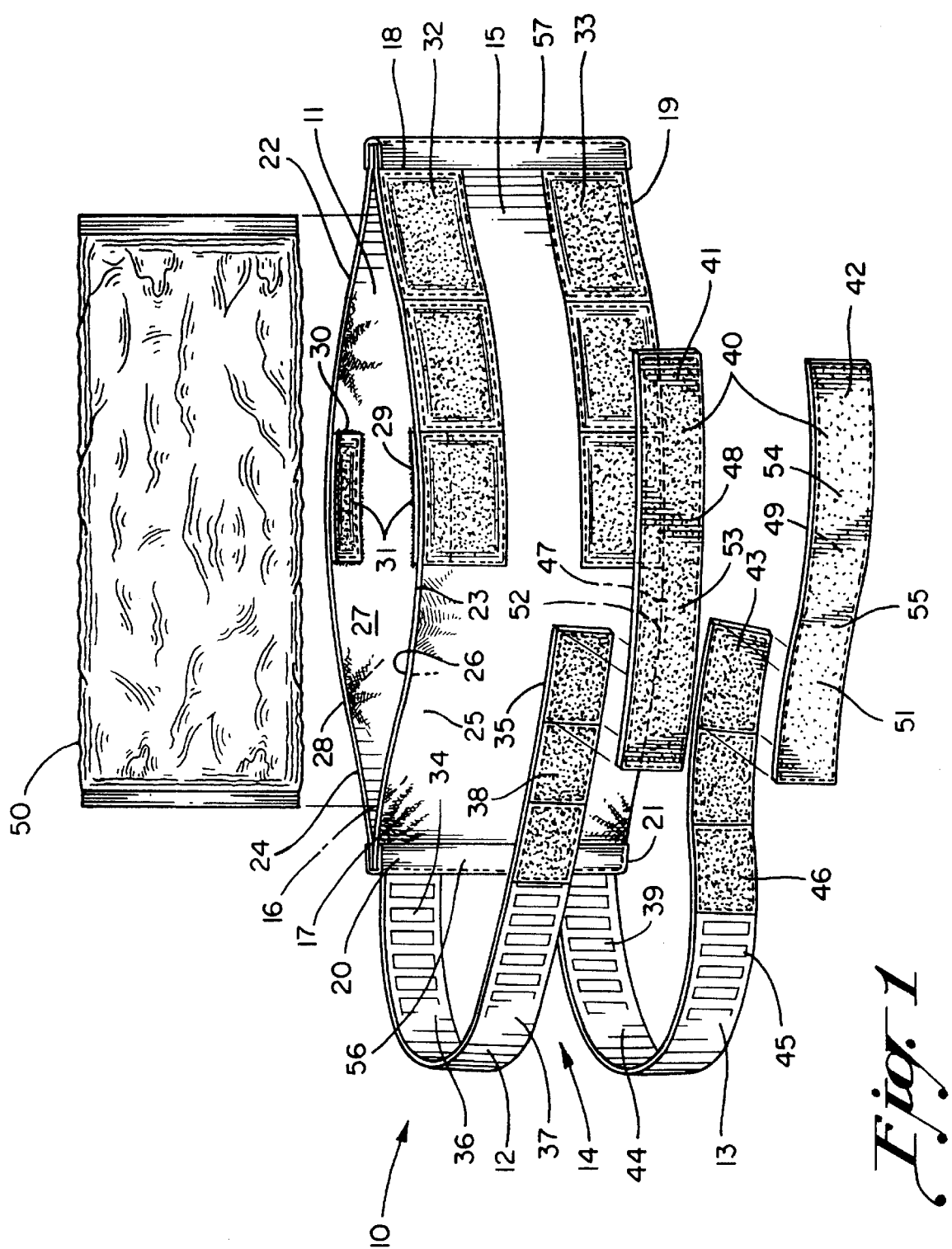
FIG. 1 is an exploded perspective view of an elasticized pressure binder and pack positioner with two extension straps and a pack.
Figures 4A, 4B:
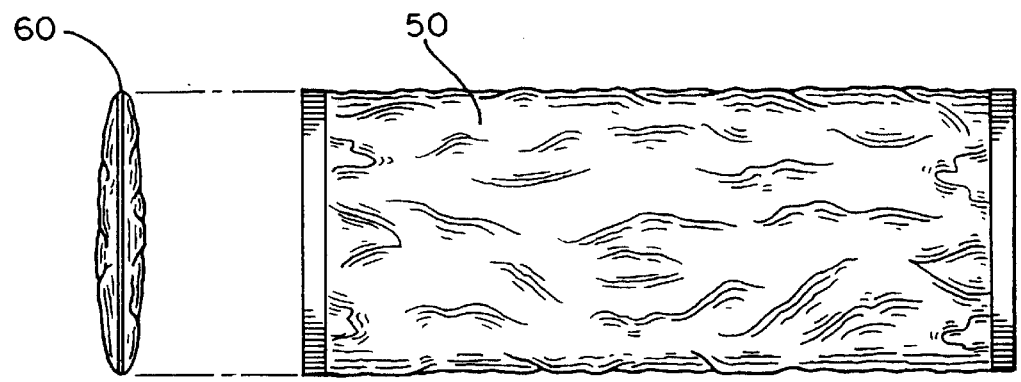
FIG. 4(a) is a side elevation view of a pack that can be pocketed by the elasticized pressure binder and pack positioner.
FIG. 4(b) is a front elevation view of a pack that can be pocketed by the elasticized pressure binder and pack positioner.

Referring now to FIG. 1, which is an exploded perspective view of the elasticized pressure binder and pack positioner 10 with a pair of elongated extension straps 40 and a pack 50. The elasticized pressure binder and pack positioner 10 is capable of pocketing various cold or hot packs 50. FIG. 4 presents both a front elevation view and the side view 60 of the cold or hot pack 50 which can be used in the current invention. The elasticized pressure binder and pack positioner 10 comprises a pocket 11, a pair of elongated elasticized straps 14, which include a first elongated. elasticized strap 12, and a second elongated elasticized strap 13. Both the first elongated elasticized strap 12 and the second elongated elasticized strap 13 can be extended by a first elongated extension strap 41 and a second elongated extension strap 42. In the preferred embodiment of the current invention, both the first elongated elasticized strap 12 and the second elongated elasticized strap 13 are seventeen inches in length and are capable of extending up to twenty-eight inches in length under tension. Therefore, it is usually capable of securing the elasticized pressure binder and pack positioner 10 to most parts of a human body. If it is necessary, one or more pairs of the elongated extension straps 40 can be used to extend the pair of elongated elasticized straps 14 to fit onto various parts of a human body having larger sizes. Due to the extension nature of both the first elongated elasticized strap 12 and the second elongated elasticized strap 13, a user can adjust the elasticized pressure binder and pack positioner 10 to provide needed pressure to a chosen body part, to which the elasticized pressure binder and pack positioner 10 is applied.

Figures 2A, 2B, 2C:
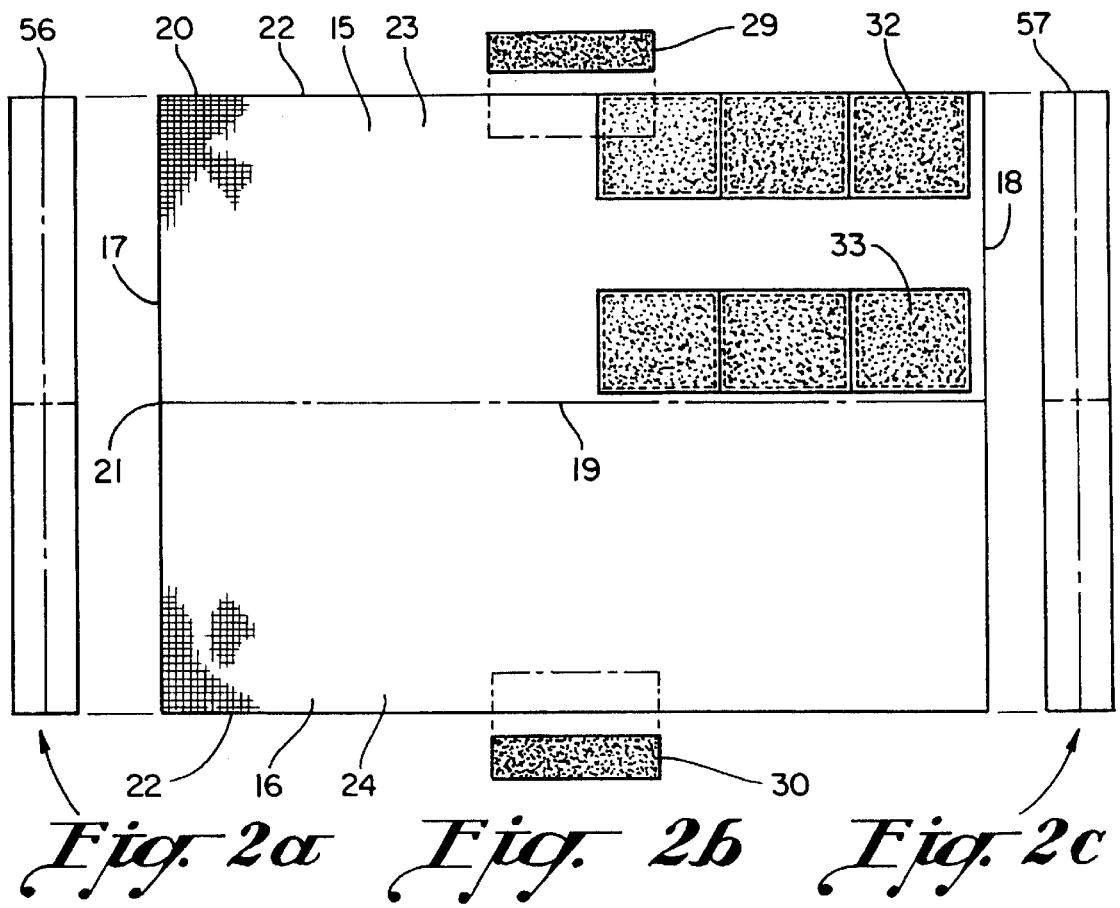
FIG. 2 is an exploded elevation view of a pocket of the elasticized pressure binder and pack positioner before being assembled.
Figure 3:
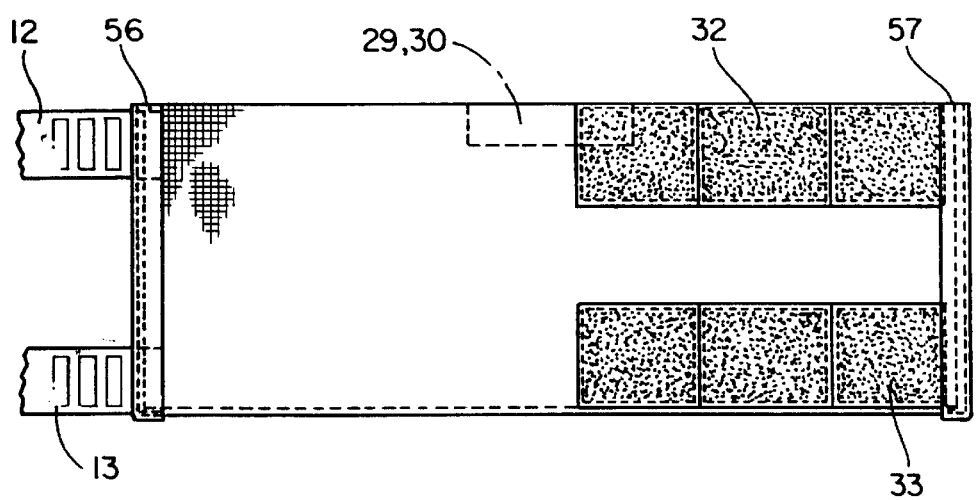
FIG. 3 is a fragmentary elevation view of the pocket of the elasticized pressure binder and pack positioner after being assembled.

Referring to FIGS. 1–3, the pocket 11 has a front side 15 and a back side 16. The pocket 11 has a first closed edge 17 with a first end 20 and a second end 21, a second closed edge 18, a third closed edge 19, and an open edge 22. The first closed edge 17 is covered by a first bias tape 56. The second closed edge 18 is covered by a second bias tape 57. Both the first bias tape 56 and the second bias tape 57 make the pocket 11 stronger, and difficult to be broken by the weight of the pack 50. The open edge 22 has a first piece 23 and a second piece 24. The first piece 23 has a first side 25 and a second side 26. The second piece 24 has a third side 27 and a fourth side 28. The second side 26 has a first portion 29 of a first hook and loop fastener structure 31, which is usually known as VELCRO brand hook and loop fastening structure. The third side 27 has a second portion 30 of the first hook and loop fastener structure 3 1. The first portion 29 of the first hook and loop fastener structure 31 and the second portion 30 of the first hook and loop fastener structure 31 are capable of closing the open edge 22 and keeping the open edge 22 closed. Various methods can be used to close the open edge 22. A zipper can be used as a method to close the open edge 22 as well. The front side 15 has a first piece of a first portion of a second hook and loop fastener structure 32 close to the open edge 22 and the second closed edge 18 and a second piece of the first portion of the second hook and loop fastener structure 33 close to the second closed edge 18 and the closed edge 19. Both the first piece 32 and the second piece of the first portion of the second hook and loop fastener structure 33 are identical. In the preferred embodiment of the current invention, both first piece 32 and fastener structure 33 comprise the hook portion of VELCRO brand hook and loop fastener structure.

Referring now to FIG. 1, the first elongated elasticized strap 12 is made of elasticized material. In the preferred embodiment of the current invention, the first elongated elasticized strap 12 is seventeen inches in length, and is capable of extending up to twenty-eight inches in length under tension. The first elongated elasticized strap 12 has a first strap end 34, a second strap end 35, a first strap side 36 and a second strap side 37. The first strap end 34 is attached onto the first end 17. The preferred method of attachment is stitching. The second strap side 37 has a first piece of a second portion of the second hook and loop fastener structure 38 at the second strap end 35. In the preferred embodiment of the current invention, the first piece of the second portion of the second hook and loop fastener structure 38 is loop portion of VELCRO brand hook and loop fastening structure. The first piece of the second portion of the second hook and loop fastener structure 38 is capable of attaching to and detaching from the first piece of the first portion of the second hook and loop fastener structure 32.

The second elongated elasticized strap 13 is identical to the first elongated elasticized strap 12. In the preferred embodiment of the current invention, the second elongated elasticized strap 13 is seventeen inches in length, and is capable of extending up to twenty-eight inches in length under tension. The second elongated elasticized strap 13 has a third strap end 39, a fourth strap end 43, a third strap side 44 and a fourth strap side 45. The third strap end 39 is affixed to the second end 21. Although any method can be used to affix the third strap end 39 to the second end 21, the third strap end 39 is sewed onto the second end 21 in the preferred embodiment. The fourth strap side 45 has a second piece of the second portion of the second hook and loop fastener structure 46 at the fourth strap end 43. In the preferred embodiment of the current invention, the second piece of the second portion of the second hook and loop fastener structure 46 is capable of attaching to and detaching from the second piece of the first portion of the second hook and loop fastener structure 33.

Figure 5:
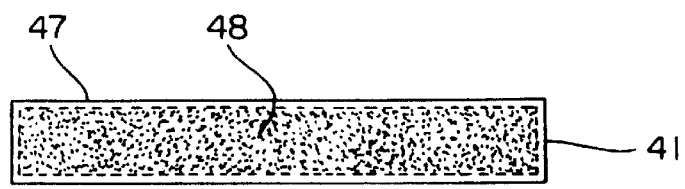
FIG. 5 is an elevation view of an elongated elasticized strap.
Figure 6:
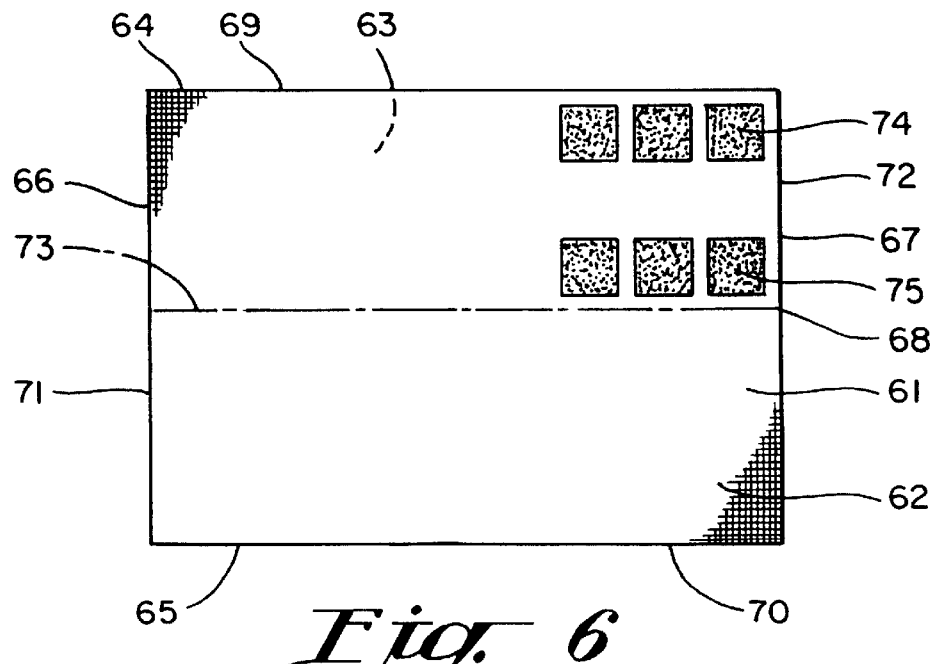
FIG. 6 is a front elevation view of a rectangular fabric, which can be assembled into the pocket of the elasticized pressure binder and pack positioner.
Figure 7:
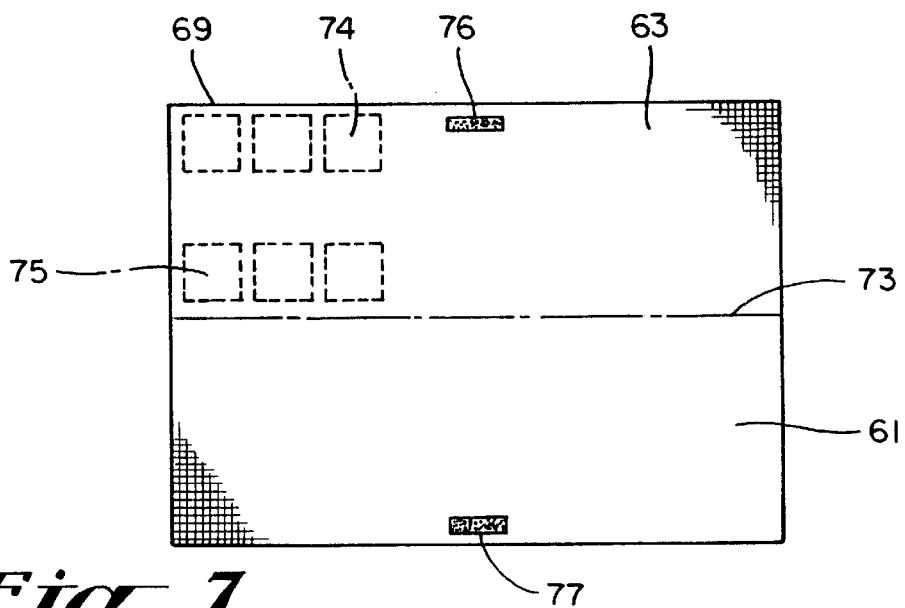
FIG. 7 is a rear elevation view of a rectangular fabric, which can be assembled into the pocket of the elasticized pressure binder and pack positioner.
Figure 8:
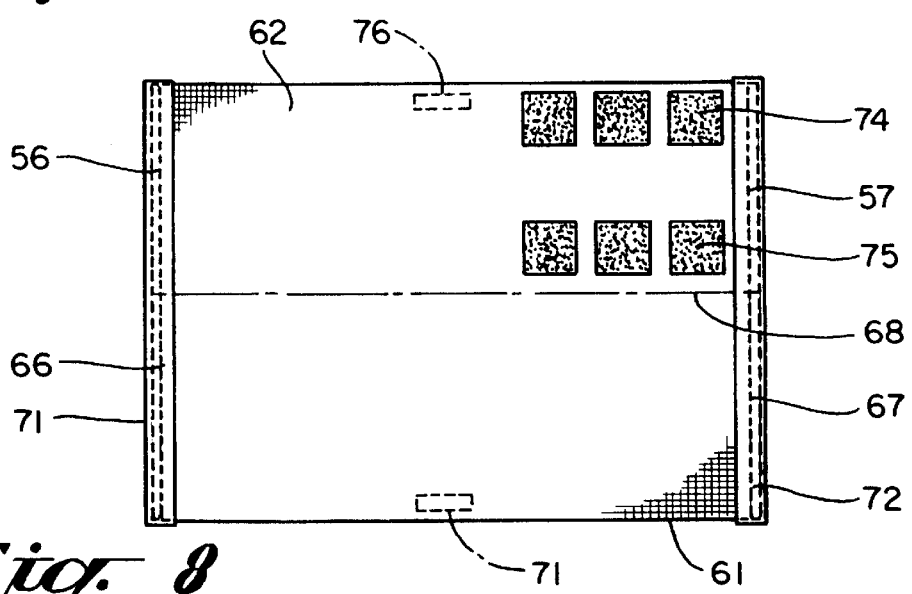
FIG. 8 is a front elevation view of the rectangular fabric with two vertical sides being covered by bias tapes.
Figure 9:
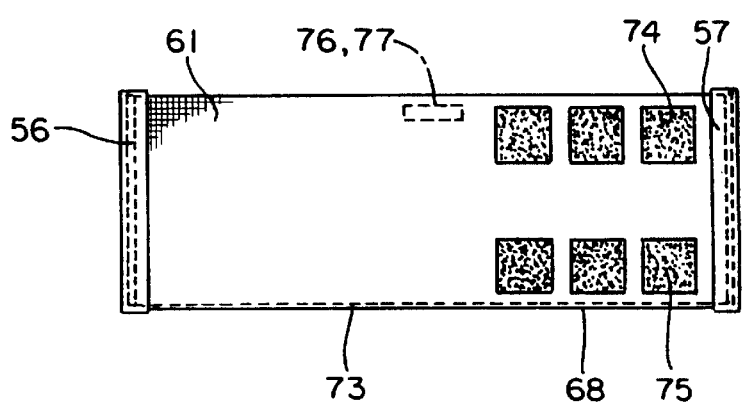
FIG. 9 is a front elevation view of the pocket.
Figure 14:
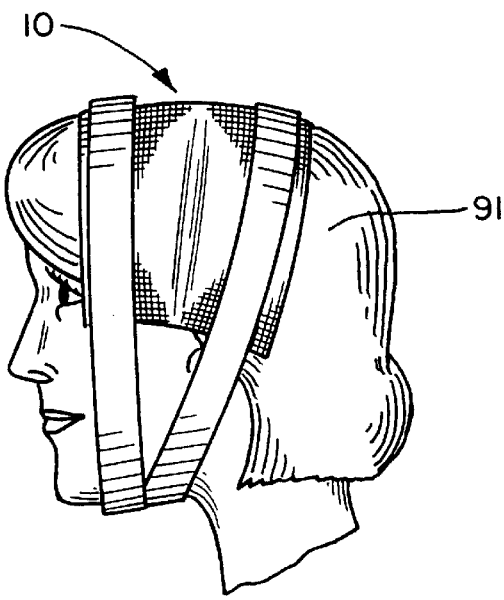
FIG. 14 is a side elevation of the present elasticized pressure binder and pack positioner being used on the head of a person.
Figure 15:
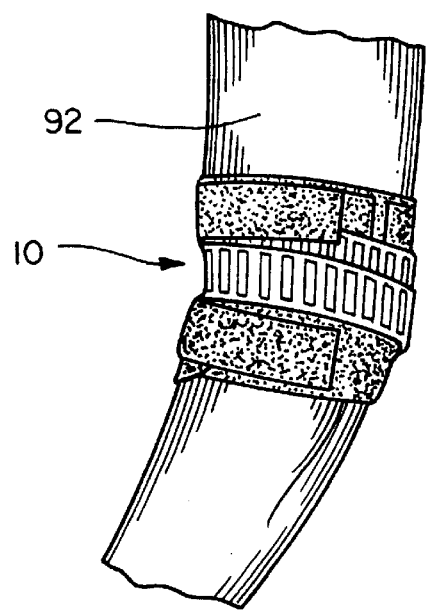
FIG. 15 is a side elevation view of the elasticized pressure binder and pack positioner being used on an elbow of a person.
Figure 16:
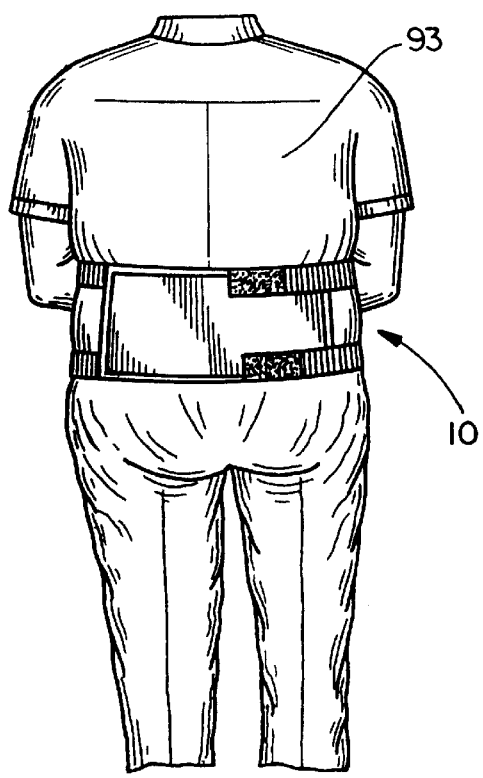
FIG. 16 is a rear view of the elasticized pressure binder and pack positioner being used about a person's waist with the pack applied to a person's back.
Figure 17:
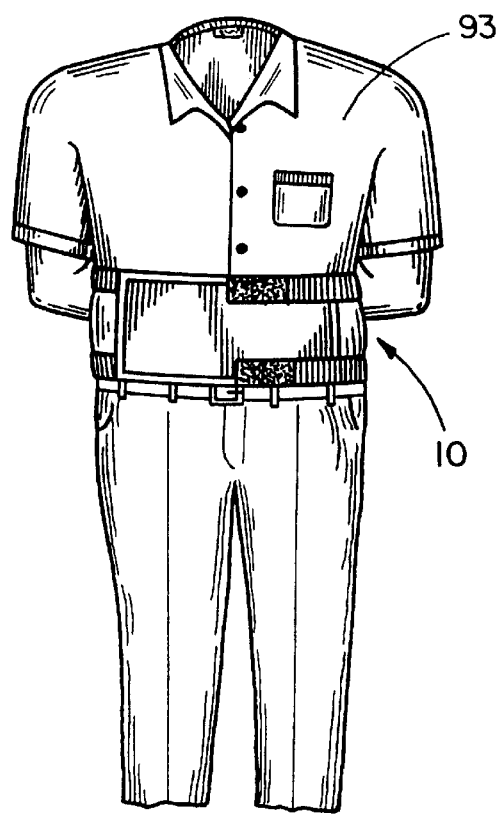
FIG. 17 is a front view of the elasticized pressure binder and pack positioner being used about a person's waist with the pack being applied to a midsection of the body of a person.

Referring now to FIGS. 1 and 5. The first elongated extension strap 41 has a fifth strap side 47 and a sixth strap side 48. The fifth strap side 47 is a first portion of a fourth hook and loop fastener structure 52. The sixth side 48 is a second portion of the fourth hook and loop fastener structure 53. The first portion of the fourth hook and loop fastener structure 52 is capable of attaching the first elongated extension strap 41 to and detaching the first elongated extension strap 41 from the first piece of the second portion of the second hook and loop fastener structure 38. The second portion of the fourth hook and loop fastener structure 53 is capable of attaching to and detaching from the first piece of the first portion of the second hook and loop fastener structure 32.

The second elongated extension strap 42 is identical to the first elongated extension strap 41. The second elongated extension strap 42 has a seventh strap side 49 and an eighth strap side 51. The seventh strap side 49 is a first portion of a fifth hook and loop fastener structure 54. The eighth side 51 is a second portion of the fifth hook and loop fastener structure 55. The first portion of the fifth hook and loop fastener structure 54 is capable of attaching the second elongated extension strap 42 to and detaching the second elongated extension strap 42 from the second piece of the second portion of the second hook and loop fastener structure 46. The second portion of the fifth hook and loop fastener structure 55 is capable of attaching to and detaching from the second piece of the first portion of the second hook and loop fastener structure 33.

The pocket 11, along with the pair of elongated elasticized straps 14 and the pair of elongated extension straps 40 enable the elasticized pressure binder and pack positioner 10 to be used on various parts of a human body.

In the preferred embodiment of the current invention, the first piece of the first portion of the second hook and loop fastener structure 32, the second piece of the first portion of the second hook and loop fastener structure 33, the first portion of the fourth hook and loop fastener structure 52, and the first portion of the fifth hook and loop fastener structure 54 are all hook type of hook and loop fastener structure. The first piece of the second portion of the second hook and loop fastener structure 38, the second piece of the second portion of the second hook and loop fastener structure 46, the second portion of the fourth hook and loop fastener structure 53, and the second portion of the fifth hook and loop fastener structure 55 are all loop type of hook and loop fastener structure.

The current invention also discloses a method of manufacturing the elasticized pressure binder and pack positioner 10, which is capable of being comfortably affixed to various different parts of a human body.

Referring now to FIGS. 6–13, which provide the details of manufacturing the elasticized pressure binder and pack positioner 10. The method of manufacture comprises the following steps:

Step 1 involves providing a rectangular fabric 61, which is capable of securely holding certain weight. In the preferred embodiment of the current invention, the rectangular fabric 61 is capable of holding at least a pound of weight. The rectangular fabric 61 has a first side 62 and a second side 63. The first side 61 has a first horizontal edge 64, a second horizontal edge 65, a first vertical edge 66, a second vertical edge 67, and a first middle horizontal line 68. The first middle horizontal line 68 is located in the middle of the first side 62 and is parallel to both the first horizontal edge 64 and the second horizontal edge 65. The second side 63 has a third horizontal edge 69, a fourth horizontal edge 70, a third vertical edge 71, a fourth vertical edge 72 and a second middle horizontal line 73. The second middle horizontal line 73 is located in the middle of the second side 63, and is parallel to both the third horizontal edge 69 and the fourth horizontal edge 70.

Step 2 involves providing a first hook portion of a hook and loop fastener structure 74.

Step 3 involves stitching the first hook portion of the hook and loop fastener structure 74 onto the first side 62 of the rectangular fabric 61 leaving three quarters of an inch space between the first hook portion of the hook and loop fastener structure 74 and the first horizontal edge 64 and leaving three quarters of an inch space between the first hook portion of the hook and loop fastener structure 74 and the second vertical edge 67. The first hook portion of the hook and loop fastener structure 74 can either be a single piece or a plurality of pieces. In the preferred embodiment of the current invention, three pieces of the hook portion of VELCRO brand hook and loop fastening structures are used.

Step 4 involves providing a second hook portion of the hook and loop fastener structure 75.

Step 5 involves stitching the second hook portion of the hook and loop fastener structure 75 onto the first side 62 of the rectangular fabric 61 leaving three quarters of an inch space between the second hook portion of the hook and loop fastener structure 75 and the first middle horizontal line 68, and leaving three quarters of an inch space between the second hook portion of the hook and loop fastener structure 75 and the second vertical edge 67. The second hook portion of the hook and loop fastener structure 75 can either be a single piece or a plurality of pieces.

Step 6 involves providing a third hook portion of the hook and loop fastener structure 76 and a third loop portion of the hook and loop fastener structure 77.

Step 7 involves sewing the third hook portion of the hook and loop fastener structure 76 onto the second side 63 of the rectangular fabric 61 at the middle of the third horizontal edge 74 leaving three quarters of an inch space between the third hook portion of the hook and loop fastener structure 76 and the third horizontal edge 69.

Step 8 involves stitching the third loop portion of the hook and loop fastener structure 77 onto the second side 63 of the rectangular fabric 61 at the middle of the fourth horizontal edge 70 leaving three quarters of an inch space between the third loop portion of the hook and loop fastener structure 77 and the fourth horizontal edge 70.

Step 9 involves providing a first bias tape 56 and a second bias tape 57.

Step 10 involves stitching the first bias tape 56 onto the first vertical edge 66 and the fourth vertical edge 71. The first bias tape encapsulates both the first vertical edge 66 and the fourth vertical edge 71.

Step 11 involves stitching the second bias tape 57 onto the second vertical edge 67 and the third vertical edge 72. The second bias tape encapsulates both the second vertical edge 67 and the third vertical edge 72.

Step 12 involves folding the rectangular fabric 61 in half horizontally along with the second middle horizontal edge 73, ensuring that the third hook portion of the hook and loop fastener structure 76 faces the third loop portion of the hook and loop fastener structure 77.

Step 13 involves stitching the third vertical edge 72 together to create a first closed edge 17 with a first end 20 and a second end 21.

Step 14 involves providing a first elongated elasticized strap 12 having a first strap side 83, a second strap side 84, a first strap end 34 and a second strap end 35.

Step 15 involves providing a second elongated elasticized strap 13 having a third strap side 85, a fourth strap side 86, a third strap end 39 and a fourth strap end 43.

Step 16 involves stitching the first strap end 34 and the third strap end 39 onto the fourth vertical edge 71. The first strap end 34 is positioned three quarters of an inch away from the third horizontal edge 69 and the fourth horizontal edge 70. The third strap end 34 is also positioned three quarters of an inch away from the second middle horizontal line 73. The fourth vertical edge 71 is then sewn together to create a second closed edge 18.

Step 17 involves providing a first loop portion of the hook and loop fastener structure 78. The first loop portion of the hook and loop fastener structure 78 has a first flat side 79 and a first loop side 80. The first loop portion of the hook and loop fastener structure 78 has a first loop portion edge 81 and a second loop portion edge 82.

Step 18 involves positioning the first loop portion of the hook and loop fastener structure 78 on the first strap side 83 at the second strap end 35, ensuring that the first loop side 80 faces the first strap side 83.

Step 19 involves stitching the first loop portion edge 81 onto the second strap end 35.

Step 20 involves flipping the first loop portion of the hook and loop fastener structure 78 over the second strap end 35.

Step 21 involves stitching the first loop portion of the hook and loop fastener structure 78 onto the second strap side 84.

Step 22 involves providing a second loop portion of the hook and loop fastener structure 85; and Repeat steps 18 to 21.

The first elongated elasticized strap 12 can be extended by adding a first extension strap 41. The first extension strap 41 has a first hook side of the hook and loop fastener structure 47 and a first loop side of the hook and loop fastener structure 48. The second elongated elasticized strap 13 can be extended by adding a second extension strap 42. The second extension strap 42 is identical to the first elongated elasticized strap 12.

Referring now to FIGS. 14 to 17, which present various uses of the present illustrated invention of the elasticized pressure binder and pack positioner 10. The elasticized pressure binder and pack positioner 10 can be used to add pressure or securely position a hot or cold pack onto the head 91 to reduce the headaches. The elasticized pressure binder and pack positioner 10 can also be used to securely position a hot or cold pack onto the jaw to ease jaw pain. The nature of both the first elongated elasticized strap 13 and the second elongated elasticized strap 14 provides the user of the elasticized pressure binder and pack positioner 10 with the ability to apply electively different degrees of pressure to the impact area of the elasticized pressure binder and pack positioner 10. The illustrated positioner embodying the present invention can also be used on the elbow 92, and on the waist 93 of a human body. When the elasticized binder and pack positioner 10 is used on a person's back, the pair of the elongated elasticized straps 14 will not weaken back muscles with long-term use. The elasticized pressure binder and pack positioner 10 can be used to replace pillow and other methods to splint abdominal incisions from traditional hysterectomy, abdominoplasty, liposuction, etc. The elasticized pressure binder and pack positioner 10 is very easy to use, and encourages post-operation activities to prevent sedentary complications, such as atelectasis and pneumonia. The elasticized pressure binder and pack positioner 10 provides the user with comfort and needed pressure on the needed body area, and enables the patient to follow a surgeon's instructions to cough, breathe deeply, and ambulate. The elasticized pressure binder and pack positioner 10 has a paneled construction to permit full range of motion. The elasticized pressure binder and pack positioner 10 is designed to prevent riding, roping and folding over when it is being used on any human body part. The elasticized pressure binder and pack positioner 10 can be extended by using the pair of extension straps 40, thus enabling the positioner to be applied to various body parts with different dimensions. Due to the nature of the elasticity of the pair of elongated elasticized straps 14, a user of the application of the present invention 10 will have the capability to adjust the pressure of the elasticized pressure binder and pack positioner to the applied area of the user's body. The structure of the elasticized pressure binder and pack positioner 10 permits quick and easy access to the wound site without tearing off tape, and requires no cutting, taping or additional supplies or tools. Because a user is capable of securely positioning a pack 50 to an intended area of a body part, the elasticized pressure binder and pack positioner provides the user a better chance to recover from various injuries and relief from various pains. The fully elasticized construction of the elasticized pressure binder and pack positioner 10 enables desired compression and perfect fit, resulting in a conformable fit that is non restrictive.

Hence, the present invention provides an improved pressure binder and pack positioner, which is simple in structure, inexpensive to manufacture, easy to use, and comfortable for a user to wear.

The present invention also provides an improved pressure binder and pack positioner, which is capable of binding human body parts to intended positions with adjustable pressure.

The present invention further provides an improved pressure binder and pack positioner, which is capable of positioning a cold or hot pack at its intended position on various body parts.

The present invention still further provides an improved pressure binder and pack positioner, which is capable of providing adjustable pressure to the body part on which it is applied.

The present invention further provides an improved pressure binder and pack positioner, which is easy to manufacture.

The present invention still further provides an improved pressure binder and pack positioner, which is simple in structure.

The present invention further provides an improved pressure binder and pack positioner, which is light in weight.

The present invention still further provides a method to manufacture such an improved pressure binder and pack positioner.

It will thus be seen that the present invention can be used to replace pillow and other methods to splint abdominal incisions from traditional hysterectomy, abdominoplasty, liposuction, etc. It will be further seen that the present invention encourages post-operation activities to prevent sedentary complications, such as atelectasis and pneumonia and enables the patient to follow a surgeon's instructions to cough, breathe deeply, and ambulate. When the present invention is used on a person's back, the pair of the elongated elasticized straps will not weaken back muscles with longterm use. Further, the present invention can be quickly adjusted to accommodate edema and permits quick and easy access to a wound site without tearing off tape. The present invention further allows patients and/or clinicians to control the amount of applied pressure and requires no cutting, taping or additional supplies or tools. The fully elasticized construction of the present invention enables desired compression and perfect fit, resulting in non-restrictive comfort.

As various possible embodiments may be made in the above invention for use for different purposes and as various changes might be made in the embodiments and methods above set forth, it is understood that all of the above matters here set forth or shown in the accompanying drawings are to be interpreted as illustrative and not in a limiting sense.

I claim:

1. An elasticized pressure binder and pack positioner capable of comfortably affixing to various different part of a human being's body, said elasticized pressure binder and pack positioner comprising:

a pocket, said pocket having a front side, a back side, a first closed edge, said first closed edge having a first end and a second end, a second closed edge, a third closed edge, and an open edge, said open edge having a first piece and a second piece, said first piece having a first side and a second side, said second piece having a third side and a fourth side, said second side having a first part of a first hook and loop fastener structure, said third side having a second part of said first hook and loop fastener structure, said first part of said first hook and loop fastener structure and said second part of said first hook and loop fastener structure capable of closing said open edge and keeping said open edge closed, said front side having a first piece of a first part of a second hook and loop fastener structure close to said open edge and said second closed edge and a second piece of said first part of said second hook and loop fastener structure close to said third closed edge and said second closed edge, said first piece and said second piece of said first part of said second hook and loop fastener structure being identical;

a first elongated elasticized strap, said first elongated elasticized strap having a first strap end, a second strap end, a first strap face and a second strap face, said first strap end being affixed to said first end of said first closed edge of said pocket, said second strap face having a first piece of a second part of said second hook and loop fastener structure at said second strap end, said first elongated elasticized strap being seventeen inches in length and capable of extending up to twenty-eight inches in length under tension, said first piece of said second part of said second hook and loop fastener structure capable of attaching to and detaching from said first piece of said first part of said second hook and loop fastener structure;

a second elongated elasticized strap, said second elongated elasticized strap being identical to said first elongated elasticized strap, both said first elongated elasticized strip and said second elongated elasticized strip capable of providing needed pressure to press said pocket to any intended part of a human being without restricting moving capability of other parts of said human being, said needed pressure being adjustable according to various needs of said human being, said second elongated elasticized strap having a third strap end, a fourth strap end, a third strap face and a fourth strap face, said third strap end being affixed to said second end, said fourth strap face having a second piece of said second part of said second hook and loop fastener structure at said fourth strap end, said second elongated elasticized strap being seventeen inches in length and capable of extending up to twenty-eight inches in length under tension, said second piece of said second part of said second hook and loop fastener structure capable of attaching to and detaching from said second piece of said first part of said second hook and loop fastener structure;

a first elongated extension strap, said first elongated extension strap having a fifth strap end, a sixth strap end, a fifth strap face and a sixth strap face, said fifth strap face being a first part of a fourth hook and loop fastener structure, said sixth face being a second part of said fourth hook and loop fastener structure, said first part of said fourth hook and loop fastener structure capable of attaching said first elongated extension strap to and detaching said first elongated extension strap from said first piece of said second part of said second hook and loop fastener structure, said second part of said fourth hook and loop fastener structure capable of attaching to and detaching from said first piece of said first part of said second hook and loop fastener structure; and a second elongated extension strap, said second elongated extension strap being identical to said first elongated extension strap, said second elongated extension strap having a seventh strap end, an eighth strap end, a seventh strap face and an eighth strap face, said seventh strap face being a first part of a fifth hook and loop fastener structure, said eighth face being a second part of said fifth hook and loop fastener structure, said first part of said fifth hook and loop fastener structure capable of attaching said second elongated extension strap to and detaching said second elongated extension strap from said second piece of said second part of said second hook and loop fastener structure, said second part of said fifth hook and loop fastener structure capable of attaching to and detaching from said second piece of said first part of said second hook and loop fastener structure.

2. The elasticized pressure binder and pack positioner in claim 1, wherein said pocket is capable of pocketing a pack, said pack being a cold pack, a hot pack or a regular pack.

3. The elasticized pressure binder and pack positioner in claim 1, wherein said first elongated elasticized strap and said second elongated elasticized strap are capable of affixing said pocket to various part of a human body.

4. The elasticized pressure binder and pack positioner in claim 1, wherein said first piece of said first portion of said second hook and loop fastener structure, said second piece of said first portion of said second hook and loop fastener structure, said first portion of said fourth hook and loop fastener structure, and said first portion of said fifth hook and loop fastener structure are female type of hook and loop fastener structure.

5. The elasticized pressure binder and pack positioner in claim 1, wherein said first piece of said second portion of said second hook and loop fastener structure, said second piece of said second portion of said second hook and loop fastener structure, said second portion of said fourth hook and loop fastener structure and said second portion of said fifth hook and loop fastener structure are male type of hook and loop fastener structure.

6. The elasticized pressure binder and pack positioner in claim 1, wherein said second portion of said second hook and loop fastener structure and said second portion of said third hook and loop fastener structure are male type of loop and fastener structure.

7. A method of manufacturing an elasticized pressure binder and pack positioner capable of comfortably affixing to various different part of a human body, said method comprising:

providing a rectangular fabric, said rectangular fabric capable of securely holding at least a pound of weight, said rectangular fabric having a first face and a second face, said first face having a first horizontal edge, a second horizontal edge, a first vertical edge, a second vertical edge, and a first middle horizontal line, said first middle horizontal line located in the middle of said first face and being parallel to both said first horizontal edge and said second horizontal edge, said second face having a third horizontal edge, a fourth horizontal edge, a third vertical edge, a fourth vertical edge and a second middle horizontal line, said second middle horizontal line located in the middle of said second face and being parallel to both said third horizontal edge and said fourth horizontal edge;

providing a first hook portion of a hook and loop fastener structure;

sewing said first hook portion of said hook and loop fastener structure onto said first face of said rectangular fabric leaving three quarters of an inch space between said first hook portion and said first horizontal edge and leaving three quarters of an inch space between said first hook portion and said second vertical edge, said first hook portion being a plurality of hook portions;

providing a second hook portion of said hook and loop fastener structure;

sewing said second hook portion of said hook and loop fastener structure onto said first face of said rectangular fabric leaving three quarters of an inch space between said second hook portion and said first middle horizontal line and leaving three quarters of an inch space between said second hook portion and said second vertical edge, said second hook portion being a plurality of hook portions;

sewing a third hook portion of said hook and loop fastener structure onto said second face of said rectangular fabric at the middle of said third horizontal edge leaving three quarters of an inch space between said third hook portion and said third horizontal edge;

sewing a third loop portion of said hook and loop fastener structure onto said second face of said rectangular fabric at the middle of said fourth horizontal edge leaving three quarters of an inch of space between said third loop portion and said fourth horizontal edge;

sewing a first bias tape onto said first vertical edge and said fourth vertical edge, said first bias tape encapsulating both said first vertical edge and said fourth vertical edge;

sewing a second bias tape onto said second vertical edge and said third vertical edge, said second bias tape encapsulating both said second vertical edge and said third vertical edge;

folding said rectangular fabric in half horizontally along with said second middle horizontal edge, ensuring said third hook portion facing said third loop portion;

sewing said third vertical edge together;

providing a first elongated elasticized strap having a first end and a second end;

providing a second elongated elasticized strap having a third end and a fourth end;

sewing said first end and said third end onto said fourth vertical edge, said first end being three quarters of an inch away from said third horizontal edge and said fourth horizontal edge, said third end being three quarters of an inch away from said second middle horizontal line;

sewing said fourth vertical edge together;

providing a first loop portion of said hook and loop fastener structure;

stitching said first loop portion of said hook and loop fastener structure onto said second end;

providing a second loop portion of said hook and loop fastener structure; and stitching said second portion of said hook and loop fastener structure onto said fourth end.

8. The method of manufacturing an elasticized pressure binder and pack positioner in claim 7, wherein said first elongated elasticized strap can be extended by adding a third extension strap having a fifth end and a sixth end, said fifth end having a fourth hook portion of said hook and loop fastener structure, said sixth end having a fourth loop portion of said hook and loop fastener structure.

9. The method of manufacturing an elasticized pressure binder and pack positioner in claim 7, wherein said second elongated elasticized strap can be extended by adding a fourth extension strap having a seventh end and an eighth end, said seventh end having a fifth hook portion of said hook and loop fastener structure, said eighth end having a fifth loop portion of said hook and loop fastener structure.

10. A method of making an elasticized pressure binder and pack positioner capable of comfortably affixing to various different part of a human being's body, said method comprising:

providing a pocket with an open end and three close ends, said open end having a means for closing, said means for closing capable of closing said open end, said pocket being capable of securely holding at least a pound of weight, said pocket having a front side and a back side;

providing a hook and loop fastener structure, said hook and loop fastener structure having a hook part and a loop part;

sewing said hook part onto said front side, said hook part being a plurality of hook parts;

providing an elongated elasticized strip, said elongated elasticized strip having a first end and a second end, said elongated elasticized strip capable of providing needed pressure to press said pocket to any intended part of a human being without restricting moving capability of other parts of said human being, said needed pressure being adjustable according to various needs of said human being, said elongated elasticized strip being a plurality of elongated elasticized strips;

sewing said first end onto one of said three closed ends; and sewing said loop part onto said second end.

11. A method of using an elasticized pressure binder and pack positioner capable of being comfortably affixed to various different parts of a human body, said positioner having a pocket with an open end and three close ends, providing said open end with a means for closing, said means for closing capable of closing said open end, said pocket being capable of securely holding at least a pound of weight, providing the pocket walls with a front side and a back side; a hook and loop fastener structure having a hook portion and a loop portion; said hook portion being sewn to said front side, said hook portion being a plurality of hook portions; an elongated elasticized strip with a first end and a second end, said elongated elasticized strip including a plurality of elongated elasticized strips being sufficiently sized and shaped to allow encirclement of a body part, the improvement of wrapping free ends of the elasticized strips remote from the pocket encircling of a circumference of a body part an appropriate number of times to provide an appropriate amount of pressure to the body part to minimize development of weakened tissues and muscles by a user while the user wears the elasticized pressure binder and pack positioner.

* * * * *